US008758989B2

(12) United States Patent
Song

(10) Patent No.: US 8,758,989 B2
(45) Date of Patent: *Jun. 24, 2014

(54) ENZYMATIC DETECTION TECHNIQUES

(75) Inventor: Xuedong Song, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1319 days.

This patent is subject to a terminal disclaimer.

(21) Appl. No.: 11/399,687

(22) Filed: Apr. 6, 2006

(65) Prior Publication Data

US 2007/0238102 A1 Oct. 11, 2007

(51) Int. Cl.
C12Q 1/00 (2006.01)

(52) U.S. Cl.
USPC ........ 435/4; 435/15; 435/18; 435/23; 435/24; 435/287.7

(58) Field of Classification Search
USPC .............. 361/103, 104, 707; 338/50–53, 179, 338/198–200, 215, 220–221, 260, 325; 417/32, 45; 337/414
See application file for complete search history.

(56) References Cited

U.S. PATENT DOCUMENTS

| | | |
|---|---|---|
| 3,700,623 A | 10/1972 | Keim |
| 3,772,076 A | 11/1973 | Keim |
| 4,140,580 A | 2/1979 | Gibson et al. |
| 4,275,149 A | 6/1981 | Litman et al. |
| 4,537,657 A | 8/1985 | Keim |
| 4,614,723 A | 9/1986 | Schmidt et al. |
| 4,637,979 A | 1/1987 | Skjold et al. |
| 4,748,116 A | 5/1988 | Simonsson et al. |
| 4,806,423 A | 2/1989 | Hugl et al. |
| 4,814,271 A | 3/1989 | Hugl et al. |
| 4,859,581 A | 8/1989 | Nicolson et al. |
| 4,874,695 A | 10/1989 | Pincus |
| 5,075,077 A | 12/1991 | Durley, III et al. |
| 5,124,254 A | 6/1992 | Hewlins et al. |
| 5,252,459 A | 10/1993 | Tarcha et al. |
| 5,292,652 A | 3/1994 | Dovey et al. |
| 5,328,831 A | 7/1994 | Stewart et al. |
| 5,449,612 A | 9/1995 | Lepargneur et al. |
| 5,464,739 A | 11/1995 | Johnson et al. |
| 5,464,741 A | 11/1995 | Hendrix |
| 5,518,883 A | 5/1996 | Soini |
| 5,571,684 A | 11/1996 | Lawrence et al. |
| 5,573,909 A | 11/1996 | Singer et al. |
| 5,585,273 A | 12/1996 | Lawrence et al. |
| 5,585,279 A | 12/1996 | Davidson |
| 5,591,581 A | 1/1997 | Massey et al. |
| 5,637,509 A | 6/1997 | Hemmilä et al. |
| 5,670,381 A | 9/1997 | Jou et al. |
| 5,731,147 A | 3/1998 | Bard et al. |
| 5,786,137 A | 7/1998 | Diamond et al. |
| 5,922,537 A | 7/1999 | Ewart et al. |
| 6,004,530 A | 12/1999 | Sagner et al. |
| 6,022,698 A | 2/2000 | Chen et al. |
| 6,030,840 A | 2/2000 | Mullinax et al. |
| 6,197,537 B1 | 3/2001 | Rao et al. |
| 6,235,464 B1 | 5/2001 | Henderson et al. |
| 6,242,268 B1 | 6/2001 | Wieder et al. |
| 6,243,980 B1 | 6/2001 | Bronstein et al. |
| 6,261,779 B1 | 7/2001 | Barbera-Guillem et al. |
| 6,287,798 B1 | 9/2001 | James et al. |
| 6,306,642 B1 | 10/2001 | Nelson |
| 6,348,319 B1 | 2/2002 | Braach-Maksvytis et al. |
| 6,362,011 B1 | 3/2002 | Massey et al. |
| 6,402,918 B1 | 6/2002 | Schlenoff et al. |
| 6,444,423 B1 | 9/2002 | Meade et al. |
| 6,451,619 B1 | 9/2002 | Catt et al. |
| 6,468,741 B1 | 10/2002 | Massey et al. |
| 6,472,141 B2 | 10/2002 | Nikiforov |
| 6,485,926 B2 | 11/2002 | Nemori et al. |
| 6,528,321 B1 | 3/2003 | Fitzgerald et al. |
| 6,582,930 B1 | 6/2003 | Ponomarev et al. |
| 6,585,939 B1 | 7/2003 | Dapprich |
| 6,613,583 B1 | 9/2003 | Richter et al. |
| 6,623,955 B2 | 9/2003 | Matner et al. |
| 7,041,469 B2 | 5/2006 | Lawrence et al. |
| 7,094,528 B2 | 8/2006 | Song et al. |
| 7,575,887 B2 * | 8/2009 | Song ............................. 435/23 |

(Continued)

FOREIGN PATENT DOCUMENTS

| | | |
|---|---|---|
| EP | 1998 0864864 A1 | 9/1998 |
| WO | WO 97 9714028 | 4/1997 |

(Continued)

OTHER PUBLICATIONS

L.J. Jones et al.—Quenched BODIPY Dye-Labeled Casein Substrates for the Assay of Protease Activity by Direct Fluorescence Measurement—Published, *Analytical Biochemistry* 251, 144-152 (1997) Article No. AB972259.

(Continued)

*Primary Examiner* — Satyendra Singh

(74) *Attorney, Agent, or Firm* — Dority & Manning, P.A.

(57) ABSTRACT

A diagnostic test kit for detecting the presence or quantity of an enzyme or enzyme inhibitor is provided. The diagnostic kit utilizes substrate conjugates to facilitate the detection of the enzyme or enzyme inhibitor via direct detection of the substrate and/or a product formed in an enzyme-catalyzed reaction of the substrate. The substrate conjugates include a substrate joined (e.g., covalently bonded, physically adsorbed, etc.) to a reporter. In one embodiment, for example, a peptide, protein, or glycoprotein substrate is joined to a reporter (e.g., dyed latex particle). In this embodiment, the substrate provides a cleavage target for an enzyme. Specifically, upon contacting the substrate conjugate, the enzyme catalyzes a reaction with the substrate and forms a product conjugate that includes the product of the enzyme catalyzed reaction joined to the reporter. The signal exhibited by the reporters may then be used to indicate the presence or quantity of an enzyme or enzyme inhibitor within the test sample.

9 Claims, 4 Drawing Sheets

(56) References Cited

U.S. PATENT DOCUMENTS

| | | | |
|---|---|---|---|
| 2001/0046668 A1 | 11/2001 | Levine et al. |
| 2002/0127623 A1 | 9/2002 | Minshull et al. |
| 2003/0073147 A1 | 4/2003 | Alderete et al. |
| 2003/0108978 A1 | 6/2003 | Ciambrone et al. |
| 2003/0119073 A1 | 6/2003 | Quirk et al. |
| 2003/0119202 A1 | 6/2003 | Kaylor et al. |
| 2003/0119204 A1 | 6/2003 | Wei et al. |
| 2003/0124739 A1 | 7/2003 | Song et al. |
| 2004/0002110 A1 | 1/2004 | Boga et al. |
| 2004/0029205 A1 | 2/2004 | Small, Jr. et al. |
| 2004/0043502 A1 | 3/2004 | Song et al. |
| 2004/0043507 A1 | 3/2004 | Song et al. |
| 2004/0043511 A1 | 3/2004 | Song et al. |
| 2004/0043512 A1 | 3/2004 | Song et al. |
| 2004/0081971 A1 | 4/2004 | Yue et al. |
| 2004/0106190 A1 | 6/2004 | Yang et al. |
| 2004/0121334 A1 | 6/2004 | Wei et al. |
| 2004/0121480 A1 | 6/2004 | Wei |
| 2005/0112703 A1 | 5/2005 | Song |
| 2005/0112780 A1 | 5/2005 | Song |
| 2005/0124072 A1 | 6/2005 | Boga |
| 2005/0136529 A1 | 6/2005 | Yang et al. |
| 2005/0136550 A1 | 6/2005 | Yang et al. |
| 2005/0191704 A1 | 9/2005 | Boga et al. |
| 2005/0220712 A1 | 10/2005 | Wright et al. |
| 2005/0233368 A1 | 10/2005 | Beall et al. |
| 2005/0243321 A1 | 11/2005 | Cohen et al. |
| 2005/0244643 A1 | 11/2005 | Song et al. |
| 2006/0003336 A1 | 1/2006 | Song et al. |
| 2006/0003394 A1 | 1/2006 | Song |
| 2006/0019265 A1 | 1/2006 | Song et al. |
| 2006/0057661 A1 | 3/2006 | Song et al. |
| 2006/0127459 A1 | 6/2006 | Huang et al. |
| 2007/0048182 A1 | 3/2007 | Song et al. |
| 2007/0048807 A1 | 3/2007 | Song |
| 2007/0048815 A1 | 3/2007 | Song |
| 2007/0048816 A1 | 3/2007 | Song |
| 2007/0134747 A1 | 6/2007 | DiGiammarino et al. |

FOREIGN PATENT DOCUMENTS

| | | |
|---|---|---|
| WO | WO 03023051 A2 | 3/2003 |
| WO | WO 03023051 A3 | 3/2003 |
| WO | WO 2005/066359 A1 | 7/2005 |
| WO | WO 2006 079826 A1 | 8/2006 |
| WO | WO 2007 096637 A1 | 8/2007 |
| WO | WO 2007 128980 A1 | 11/2007 |

OTHER PUBLICATIONS

J.M. Steiner et al.—Development and analytic validation of an enzyme-linked immunosorbent assay for the measurement of canine pancreatic lipase immunoreactivity in serum—Published, *The Canadian Journal of Veterinary Research* 2003; 67:175-182.

H. Rahimi et al.—Monoclonal antibodies against *Candida rugosa* lipase—Published, *Journal of Molecular Catalysts B: Enzymatic* 28 (2004) 71-74.

D.A. Schofield et al.—Differential *Candida albicans* lipase gene expression during alimentary tract colonization and infection—Published, *FEMS Microbiology Letters* 244 (2005) 359-365.

F. Stehr et al.,—Expression analysis of the *Candida albicans* lipase gene family during experimental infections and in patient samples—Published, *FEMS Yeast Research* 4 (2004) 401-408.

Englert et al.—Layered Expression Scanning: Rapid Molecular Profiling of Tumor Samples—Published, *Cancer Research* 60, 1526-1530, Mar. 15, 2000.

A.W. Kusterbeck et al.—Use of the USDT flow immunosensor for quantitation of benzoylecgonine in urine—Published, *Elsevier Science Limited, Biosensors & Bioelectronics* vol. 11 No. 8 pp. 725-734, 1996.

D.J. Pritchard et al.—Simultaneous determination of follicle stimulating hormone and luteinising hormone using multianalyte immunosensor—Published, *Elsevier, Analytica Chimica Acta* 310 (1995) 251-256.

L.M. Golub et al.—A matrix metalloproteinase inhibitor reduces bone-type collagen degradation fragments and specific collagenases in gingival crevicular fluid during adult periodontitis—Published, *Inflamm. res.* 46 (1997) 310-319.

K. Brew et al.—Tissue inbibitors of metalloproteinases: evolution, structure and function—Published, *Elsevier—Biochimica et Biophysica Acta* 1477 (2000) 267-283.

B. Stratmann et al.—MMP-TIMP interaction depends on residue 2 in TIMP-4—Published, *FEBS Letters* 507 (2001) 285-287.

Osmanağaoğlu et al.—*Identification of Different Candida Species Isolated in Various Hospitals in Ankara by Fungichrom Test Kit and Their Differentiation by SED-PAGE*, Turk. J. Med. Sci., vol. 30, 2000, pp. 355-358.

Lorenz et al.—*Transcriptional Response of Candida albicans upon Internalization by Macrophages*, Eukaryotic Cell, vol. 3. No. 5, Oct. 2004, pp. 1076-1087.

Article—*A New Tetradentate β-Diketonate-Europium Chelate That Can Be Covalently Bound to Proteins for Time-Resolved Fluoroimmunoassay*, Yuan et al., Analytical Chemistry, vol. 70, No. 3, Feb. 1, 1998, pp. 596-601.

Article—*One-step all-in-one dry reagent immunoassays with fluorescent europium chelate label and time-resolved fluorometry*, Lövgren et al., Clinical Chemistry, vol. 42, No. 8, 1996, pp. 1196-1201.

U.S. Appl. No. 11/119,262, filed Apr. 29, 2005, Song et al., Assay Devices Having Detection Capabilities within the Hook Effect Region.

U.S. Appl. No. 11/094,498, filed Mar. 30, 2005, Song et al., Diagnostic Test Kits Employing and Internal Calibration System.

U.S. Appl. No. 11/217,112, filed Aug. 31, 2005, Xuedong Song, Diagnostic Test Kits with Improved Detection Accuracy.

U.S. Appl. No. 11/217,097, filed Aug. 31, 2005, Xuedong Song, Enzyme Detection Technique.

U.S. Appl. No. 11/217,099, filed Aug. 31, 2005, Song et al., Nitrite Detection Technique.

U.S. Appl. No. 11/301,631, filed Dec. 13, 2005, Takeuchi et al., Metering Technique for Lateral Flow Assay Devices.

U.S. Appl. No. 11/364,810, filed Feb. 28, 2006, Xuedong Song., Detection of Proteases Secreted from Pathogenic Microorgansims.

Search Report and Written Opinion for PCT/IB2007/050880, Jan. 8, 2008.

\* cited by examiner

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: synthetic
      polypeptide

<400> SEQUENCE: 1

Glu Ala Ile Tyr Ala Ala Pro Phe Ala Lys Lys Lys
 1               5                  10
```

ENZYMATIC DETECTION TECHNIQUES

BACKGROUND OF THE INVENTION

It is often desirable to determine the presence or quantity of a particular enzyme within a test sample. In some cases, the mere presence of an enzyme may, for example, indicate the existence of tissue or organ damage. Likewise, abnormal enzyme concentrations may also indicate other conditions, such as a bacterial or viral infection. For instance, proteases (e.g., aspartic proteases) and metallopeptidases are believed to increase the pathogenicity of *Candida albicans*, a microorganism that may cause candidal vaginitis ("yeast infection"). The presence or concentration of an enzyme in a test sample may also serve as a diagnostic marker for some types of cancers and other conditions. For instance, prostate-specific antigen (PSA) is a well-known marker for prostate cancer. Other examples of diagnostic markers include cathepsin B (cancer), cathepsin G (emphysema, rheumatoid arthritis, inflammation), plasminogen activator (thrombosis, chronic inflammation, cancer), and urokinase (cancer).

One conventional technique for detecting the presence of an enzyme is described in U.S. Pat. No. 6,348,319 to Braach-Maksvytis, et al. Braach-Maksvytis, et al. functions by sensing the digestion of a substrate by the enzyme. For example, FIG. 1 of Braach-Maksvytis, et al. illustrates a device 10 that includes a first zone 11 and a second zone 12. The first zone 11 is provided with polymer beads 13 (carrier) linked to streptavidin 14 (reporter) via a peptide linker 15 that is cleavable by a protease 16. Upon addition of the protease 16, the streptavidin 14 is released and passes to the second zone 12, which includes a biosensor membrane 17 that detects the presence of streptavidin through a change in the impedance of the membrane. (Col. 5, ll. 25-30). Unfortunately, however, techniques such as described by Braach-Maksvytis, et al., are far too complex and cost prohibitive for certain types of applications, such as those requiring a relatively quick diagnosis by a patient (self-diagnosis or with the aid of medical personnel).

As such, a need currently exists for a simple and inexpensive technique to accurately detect the presence of an enzyme within a test sample.

SUMMARY OF THE INVENTION

In accordance with one embodiment of the present invention, a method for detecting an enzyme, or an inhibitor thereof, within a test sample, is disclosed. The method comprises contacting a test sample with a plurality of substrate conjugates to form an incubation mixture, the substrate conjugates each comprising a substrate joined to a reporter. The substrate, while joined to the reporter, is capable of undergoing an enzyme-catalyzed reaction to form a product that is joined to the reporter. The reporter is capable of directly or indirectly generating detection signal. The method further comprises applying the incubation mixture to a chromatographic medium, the chromatographic medium defining a first detection zone within which either the substrate conjugate or the product conjugate preferentially binds. The presence or intensity of a first detection signal within the first detection zone is determined.

A first detection signal is capable of being generated within the first detection zone, such as by the reporters immobilized therein. The intensity of the first detection signal in the first detection zone may determine the presence of an enzyme or an enzyme inhibitor in the test sample. For instance, when a product conjugate is captured in the first detection zone, the intensity of the first detection signal in the first detection zone may be directly proportional to the amount of an enzyme within the test sample, and may likewise be inversely proportional to the amount of an enzyme inhibitor within the test sample. Conversely, when a substrate conjugate is captured in the first detection zone, the intensity of the first detection signal in the first detection zone may be inversely proportional to the amount of an enzyme within the test sample, and may likewise be directly proportional to the amount of an enzyme inhibitor within the test sample.

In accordance with another embodiment of the present invention, a diagnostic kit is disclosed for detecting an enzyme, or an inhibitor thereof, within a test sample. The kit comprises a plurality of substrate conjugates that each comprise a substrate joined to a reporter. In one embodiment, for example, the reporter includes a particle labeled with a detectable substance. The substrate of the substrate conjugate is capable of a reaction that is catalyzed by an enzyme to form a product that is joined to the reporter as a product conjugate. The kit further comprises a chromatographic medium (e.g., porous membrane) that is capable of being placed in communication with the test sample. The chromatographic medium defines a first detection zone within which either the product conjugate or the substrate conjugate preferentially binds. For instance, a receptive material may be immobilized within the first detection zone that has a specific binding affinity for the reaction product that remains joined to the reporter, e.g., a monoclonal antibody specific for the product that is formed during the enzyme-catalyzed reaction of the substrate. Accordingly, the product conjugate may become immobilized in the first detection zone via the specific binding of this product with the first receptive material and the presence or intensity of a detection signal generated in the first detection zone from the reporter joined to the product may be determined to indicate the presence or quantity of an enzyme or an enzyme inhibitor in the test sample.

In certain embodiments, the chromatographic medium may further comprise a second detection zone within which either the substrate conjugate or the product conjugate, but not both, is capable of being captured. For example, if the first detection zone is designed to capture the product conjugate, the second detection zone may be designed to capture the substrate conjugate, and vice versa. A second detection signal is capable of being generated within the second detection zone, such as by the reporters immobilized therein.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
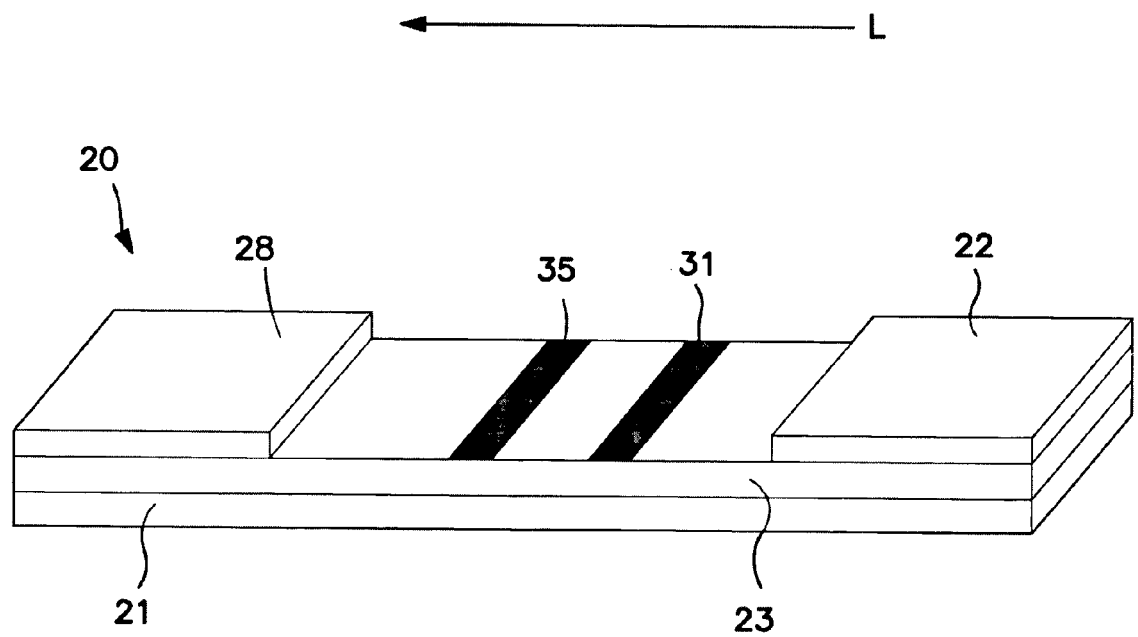
FIG. 1 is a perspective view of one embodiment of an assay device that may be used in the diagnostic test kit of the present invention.

Repeat use of reference characters in the present specification and drawings is intended to represent same or analogous features or elements of the invention.

SEQUENCE LISTING

SEQ ID NO: 1 depicts an exemplary peptide sequence that may be utilized as a substrate in detection of a protein kinase as herein described.

DETAILED DESCRIPTION OF REPRESENTATIVE EMBODIMENTS

Definitions

As used herein, the term "test sample" generally refers to a material suspected of containing an enzyme and/or enzyme inhibitor. For example, the test sample may be obtained or derived from a biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid, and so forth. Besides physiological fluids, other liquid samples may be used such as water, food products, and so forth, for the performance of environmental or food production assays. In addition, a solid material may be used as the test sample. The test sample may be used directly as obtained from a source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, etc. Moreover, it may also be beneficial to modify a solid test sample to form a liquid medium, to release the enzyme and/or enzyme inhibitor, etc.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

The present invention is generally directed to a diagnostic test kit for detecting the presence or quantity of an enzyme or an enzyme inhibitor. The diagnostic kit employs a substrate to an enzyme-catalyzed reaction to facilitate the detection of an enzyme or an enzyme inhibitor in a test sample. A substrate is presented in the form of a substrate conjugate that includes the substrate joined (e.g., covalently bonded, physically adsorbed, etc.) to a reporter. In one embodiment, for example, a peptide, protein, or glycoprotein substrate is joined to a dyed latex particle. Upon contacting the substrate conjugate, an enzyme may cleave the substrate and form a product. The reaction catalyzed by the enzyme does not, however, affect the reporter or the joining of the substrate to the reporter. Accordingly, a product of the reaction will be in the form of a product conjugate that includes the product joined to the reporter. The signal directly or indirectly generated by the reporter may be used to indicate the presence or quantity of an enzyme or enzyme inhibitor within the test sample.

Various types of enzymes may be detected in accordance with the present invention. For instance, transferases, hydrolases, lyases, and so forth, may be detected. In some embodiments, the enzyme of interest is a "hydrolase" or "hydrolytic enzyme", which refers to enzymes that catalyze hydrolytic reactions. Examples of such hydrolytic enzymes include, but are not limited to, proteases, peptidases, lipases, nucleases, homo- or hetero-oligosaccharidases, homo- or hetero-polysaccharidases, phosphatases, sulfatases, neuraminidases and esterases. In one embodiment, for example, peptidases may be detected. "Peptidases" are hydrolytic enzymes that cleave peptide bonds found in shorter peptides. Examples of peptidases include, but are not limited to, metallopeptidases; dipeptidylpeptidase I, II, or IV; and so forth. In another embodiment, proteases may be detected. "Proteases" are hydrolytic enzymes that cleave peptide bonds found in longer peptides and proteins. Examples of proteases that may be detected according to the present invention include, but are not limited to, serine proteases (e.g., chymotrypsin, trypsin, elastase, PSA, etc.), aspartic proteases (e.g., pepsin), thiol proteases (e.g., prohormone thiol proteases), metalloproteases, acid proteases, and alkaline proteases. Still other enzymes are described in U.S. Pat. No. 6,243,980 to Bronstein, et al. and 2004/0081971 to Yue, et al., which are incorporated herein in their entirety by reference thereto for all purposes.

In addition to enzymes that cleave a substrate, such as those described above, the diagnostic kit may alternatively be utilized to detect the presence of an enzyme that catalyzes the formation of a bond on the substrate. For instance, transferases, which transfer a functional group to a substrate, ligases, which covalently bond a second molecule to a substrate, or polymerases may be detected. Exemplary transferases that may be detected include kinases and methylases. For instance, kinases including protein kinases, creatine kinases, hexokinase, and so forth may be detected through detection of the phosphorylation of the substrate. Methylases such as methylase II may be detected through the addition of one or more methyl groups to the substrate.

Likewise, any of a variety of known enzyme inhibitors may also be detected in accordance with the present invention. For example, known inhibitors of hydrolytic enzymes include, but are not limited to, inhibitors of proteases, peptidases, lipases, nucleases, homo- or hetero-oligosaccharidases, homo- or hetero-polysaccharidases, phosphatases, sulfatases, neuraminidases and esterases. Protease inhibitors may include, for instance, aspartic protease inhibitors, serine protease inhibitors, thiol protease inhibitors, metalloprotease inhibitors, acid or alkaline protease inhibitors, and so forth. Some specific examples of protease inhibitors include benzamideine, indole, pepstatin, ovomacroglobulin, haloperidol, transition state mimetics, and so forth. Some specific examples of transferase inhibitors include ethacrynic acid, which inhibits glutathione S-transferase and Sarasar®, a benzocycloheptapyridyl Farnesyl Transferase Inhibitor (FTI).

As stated above, substrate conjugates are used in the present invention to detect the presence or quantity of an enzyme or enzyme inhibitor. The substrate conjugates include a substrate joined to a reporter. The term "substrate" generally refers to a substance that is chemically acted upon by or in the presence of an enzyme to form a product. The substrate may occur naturally or be synthetic. Specific types of substrates may include, for instance, proteins or glycoproteins, peptides, nucleic acids (e.g., DNA and RNA), antigens, antibodies, carbohydrates, lipids, esters, derivatives thereof, and so forth. Some suitable substrates for hydrolytic enzymes include, for instance, esters, amides, peptides, ethers, or other chemical compounds having an enzymatically-hydrolyzable bond. The enzyme-catalyzed hydrolysis reaction may, for example, result in a hydroxyl or amine compound as one product, and a free phosphate, acetate, etc., as a second product. Some suitable substrates for peptidases and/or proteases may include peptides, proteins, and/or glycoproteins, such as casein (e.g., β-casein, azocasein, etc.), albumin (e.g., bovine serum albumin (BSA)), hemoglobin, myoglobin, keratin, gelatin, insulin, proteoglycan, fibronectin, laminin, collagen, elastin, and so forth. Some suitable substrates for kinases and/or methylases may include ovalbumin, peptides, creatine, hexoses, nucleotides, nucleosides, lipids, and so forth. Still other suitable substrates are described in U.S. Pat. No. 4,748,116 to Simonsson, et al.; U.S. Pat. No. 5,786,137 to Diamond, et al.; U.S. Pat. No. 6,197,537 to Rao, et al.; and U.S. Pat. No. 6,235,464 to Henderson, et al.; U.S. Pat. No. 6,485,926 to Nemori, et al., which are incorporated herein in their entirety by reference thereto for all purposes.

The reporter may include any substance capable of directly or indirectly generating a detectable signal. Suitable detectable substances may include, for instance, chromogens; luminescent compounds (e.g., fluorescent, phosphorescent, etc.); radioactive compounds; visual compounds (e.g., latex or metallic particles, such as gold); liposomes or other vesicles containing signal-producing substances; enzymes and/or substrates, and so forth. For instance, some enzymes suitable for use as detectable substances are described in U.S. Pat. No. 4,275,149 to Litman, et al., which is incorporated herein in its entirety by reference thereto for all purposes. One example of an enzyme/substrate system is the enzyme alkaline phosphatase and the substrate nitro blue tetrazolium-5-bromo-4-chloro-3-indolyl phosphate, or derivative or analog thereof, or the substrate 4-methylumbelliferyl-phosphate. Other suitable reporters may be described in U.S. Pat. No. 5,670,381 to Jou, et al. and U.S. Pat. No. 5,252,459 to Tarcha, et al., which are incorporated herein in their entirety by reference thereto for all purposes.

In some embodiments, the reporter may contain a luminescent compound that produces an optically detectable signal. The luminescent compound may be a molecule, polymer, dendrimer, particle, and so forth. For example, suitable fluorescent molecules may include, but are not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or nonaqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart, et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis[(4,4'-carbomethoxy)-2,2'-bipyridine]2-[3-(4-methyl-2,2'-bipyridine-4-yl)propyl]-1,3-dioxolane ruthenium (II); bis(2,2'-bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid]ruthenium (II); tris(2,2'-bipyridine)ruthenium (II); (2,2'-bipyridine) [bis-bis(1,2-diphenylphosphino)ethylene]2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2,2'-bipyridine-4-yl)butane]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein in their entirety by reference thereto for all purposes.

In some cases, "time-resolved" luminescent detection techniques are utilized. Time-resolved detection involves exciting a luminescent compound with one or more short pulses of light, then typically waiting a certain time (e.g., between approximately 1 to 100 microseconds) after excitation before measuring the remaining the luminescent signal. In this manner, any short-lived phosphorescent or fluorescent background signals and scattered excitation radiation are eliminated. This ability to eliminate much of the background signals may result in sensitivities that are 2 to 4 orders greater than conventional fluorescence or phosphorescence. Thus, time-resolved detection is designed to reduce background signals from the emission source or from scattering processes (resulting from scattering of the excitation radiation) by taking advantage of the characteristics of certain luminescent materials.

To function effectively, time-resolved techniques generally require a relatively long emission lifetime for the luminescent compound. This is desired so that the compound emits its signal well after any short-lived background signals dissipate. Furthermore, a long luminescence lifetime makes it possible to use low-cost circuitry for time-gated measurements. For example, the detectable compounds may have a luminescence lifetime of greater than about 1 microsecond, in some embodiments greater than about 10 microseconds, in some embodiments greater than about 50 microseconds, and in some embodiments, from about 100 microseconds to about 1000 microseconds. In addition, the compound may also have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, one suitable type of fluorescent compound for use in time-resolved detection techniques includes lanthanide chelates of samarium (Sm (III)), dysprosium (Dy (III)), europium (Eu (III)), and terbium (Tb (III)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have exceptionally large Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent compound. In addition, these chelates have narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N, N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent compounds described above, other compounds that are suitable for use in the present invention may be described in U.S. Pat. No. 6,030,840 to Mullinax, et al.; U.S. Pat. No. 5,585,279 to Davidson; U.S. Pat. No. 5,573,909 to Singer, et al.; U.S. Pat. No. 6,242,268 to Wieder, et al.; and U.S. Pat. No. 5,637,509 to Hemmila, et al., which are incorporated herein in their entirety by reference thereto for all purposes.

As stated, the reporter may indirectly generate a detectable signal in some embodiments of the present invention. In such instances, the reporter may not specifically contain a detectable substance, but instead be capable of interacting with a detectable substance to generate a detection signal. For example, in some embodiments, the reporter may be or may include a member of a specific binding pair, such as further described herein. For example, a reporter that is or includes a member of a specific binding pair may be placed into contact with a detectable substance conjugated with another member of the specific binding pair. Thus, the reporter, which is a member of a product conjugate or a substrate conjugate, will bind to the detectable substance, and the conjugate, now including the reporter bound to the detectable substance, may then be readily detected (directly or indirectly) using techniques well known to those skilled in the art. As will be explained in more detail below, when the reporter contains a specific binding member, it is generally desired that the specific binding member is different than and has no specific binding affinity for other specific binding members as may be immobilized on the device.

Whether or not the reporter directly or indirectly generates a signal, it may contain particles (sometimes referred to as "beads" or "microbeads"). Among other things, particles enhance the ability of the reporter to travel through a chromatographic medium and become immobilized within a detection zone, such as described below. For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex particles are labeled with a fluorescent or colored dye. Although any latex particle may be used, the latex particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al. and U.S. Pat. No. 5,252,459 to Tarcha, et al. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. of Eugene, Oreg. In addition, commercially available examples of suitable colored, latex microparticles include carboxylated latex beads sold by Bangs Laboratories, Inc. of Fishers, Ind.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

The reporter may generally be attached to the substrate using any of a variety of well-known techniques. For instance, covalent attachment of the reporter to a substrate may be accomplished using carboxylic, amino, aldehyde, bromoacetyl, iodoacetyl, thiol, epoxy and other reactive functional groups, as well as residual free radicals and radical cations, through which a coupling reaction may be accomplished. A surface functional group may also be incorporated as a functionalized co-monomer because the surface of the reporter may contain a relatively high surface concentration of polar groups. In certain cases, the reporter may be capable of direct covalent bonding to a substrate without the need for further modification. It should also be understood that, besides covalent bonding, other attachment techniques, such as physical adsorption, may also be utilized in the present invention. Still other non-covalent linkage techniques may employ antibodies and/or antigens, such as secondary antibodies (e.g., avidin, streptavidin, neutravidin, and/or biotin).

One particular technique for covalently bonding a reporter to a substrate will now be described in more detail. In this particular embodiment, the substrate is β-casein, and the reporter is a dyed particle. For example, the reporter may be red carboxylated latex particles available from Molecular Probes, Inc. under the name "FluoSphere."

Figure 2:
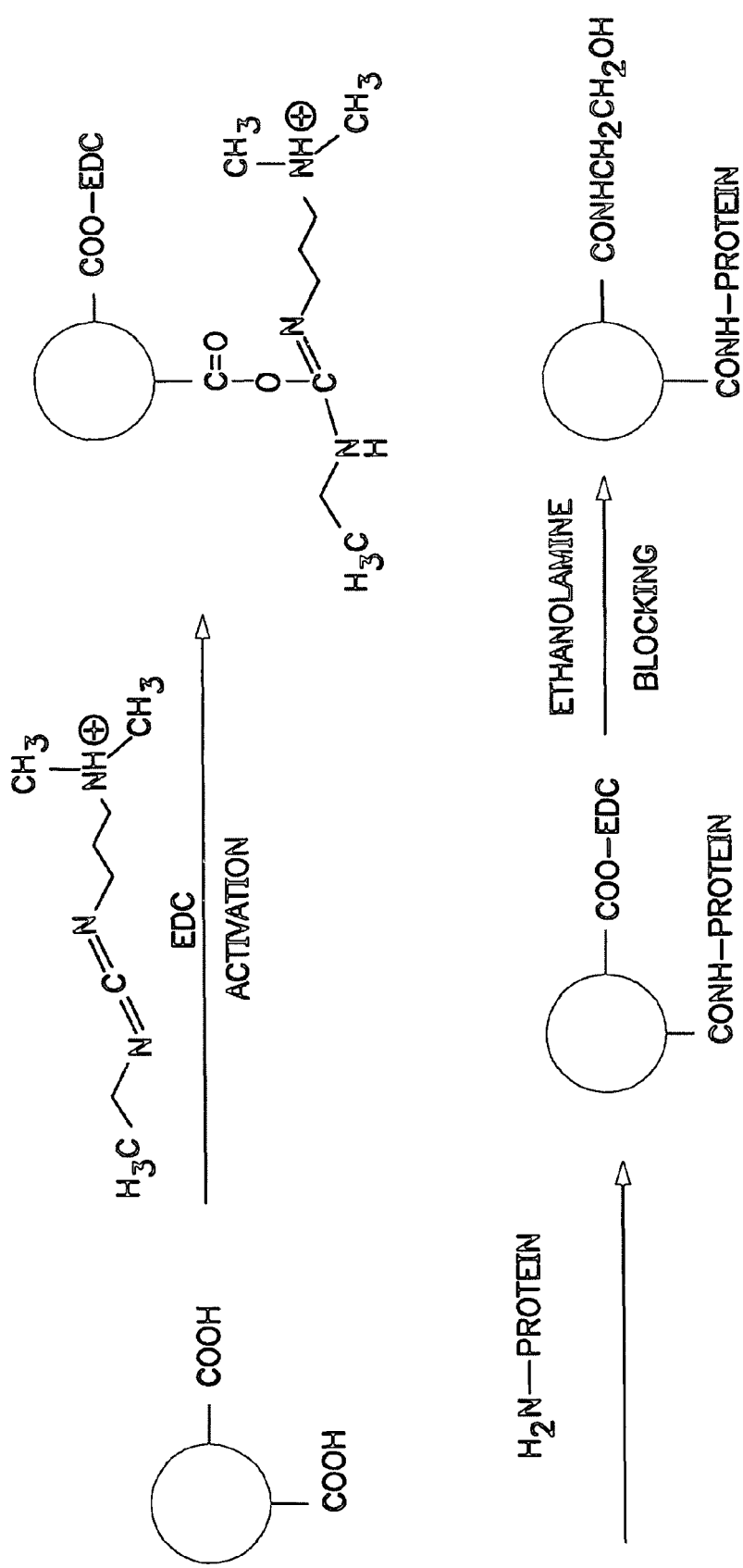
FIG. 2 is a graphical illustration of one embodiment for covalently bonding a reporter to a substrate.

To covalently conjugate the dyed particle with β-casein, the carboxylic groups on the particle surface are first activated with a carbodiimide (e.g., ethylcarbodiimide hydrochloride (EDC)), such as shown in FIG. 2. Because protein and glycoprotein substrates (e.g., β-casein) typically possess primary amine groups ($NH_2$), such as on the side chain of lysine (K) residues and/or the N-terminus of each polypeptide, the activated carboxylic acid groups may then be reacted with the primary amine ($-NH_2$) groups of the substrate to form an amide bond. This reaction may occur in a buffer, such as phosphate-buffered saline (PBS) (e.g., pH of 7.2), 2-(N-morpholino) ethane sulfonic acid (MES) (e.g., pH of 5.3), or borate buffer (e.g., pH of 8.5). If desired, the resulting substrate conjugate may then be blocked with ethanolamine, for instance, to block any remaining activated sites.

Once formed, a user may allow the test sample and any other necessary components to incubate with the substrate conjugate for a certain period of time. For example, those skilled in the art readily recognize that the time of incubation for an enzyme-catalyzed reaction depends on the activity of the enzyme of interest, which in turn depends on in part on the temperature, pH, substrate concentration, the presence of inhibitors (competitive (binds to substrate), uncompetitive (binds to enzyme-substrate complex), or noncompetitive (binds to enzyme and/or enzyme-substrate complex)), and so forth. These factors may be selectively controlled as desired to increase or decrease the incubation time. For example, the time for incubation may be greater than about 1 minute, in some embodiments from about 5 to about 50 minutes, and in some embodiments, from about 10 to about 25 minutes. Likewise, the pH may be selectively controlled to facilitate enzyme activity. For example, high levels of basic substances within a test sample may result in a pH that is too high for optimum activity of some enzymes, e.g., greater than 8. Specifically, an enzyme may possess optimum activity at a pH level of from about 3 to about 8, and in some embodiments, from about 4 to about 7. Thus, if desired, a buffer or other pH-altering compound may be employed to maintain the desired pH.

After incubation, any enzyme present within the test sample will typically react with the substrate of at least a portion of the substrate conjugates. As a result, various species may be formed, including product conjugates (reporter-product), partially reacted complexes (e.g., reporter-substrate-enzyme), unreacted substrate conjugates (reporter-substrate), and secondary reactants and products of the enzyme-catalyzed reaction. For instance, in the case of a hydrolytic enzyme, materials cleaved from the substrate conjugate during the enzyme-catalyzed cleavage reaction will be included in the incubation mixture. When considering an enzyme-catalyzed reaction in which new bonds are formed on the substrate, materials included in the incubation mixture may include other reactants involved in the reaction (e.g., ATP, methyl-donating reactants, monomers such as amino acids, and nucleotides that may be added to the substrate by a polymerase or a ligase, etc.) as well as secondary products formed in the enzyme-catalyzed reaction (e.g., ADP). Longer incubation times and greater enzyme concentrations may result in a greater concentration of product conjugates in the resulting incubation mixture.

In accordance with the present invention, the diagnostic test kit also contains an assay device that employs a chromatographic medium for chemically separating the substrate conjugates and/or the product conjugates from other species present within the incubation mixture. In contrast to other separation techniques, such as centrifugation, a chromatographic medium may simplify and reduce the costs of the resulting diagnostic test kit for many consumer applications, including those in which a disposable kit is desired.

Referring to FIG. 1, for instance, one embodiment of an assay device 20 that may be used to indicate the presence or quantity of an enzyme in accordance with the present invention will now be described in more detail. As shown, the assay device 20 contains a chromatographic medium 23 optionally carried by a support 21. The chromatographic medium 23 may be made from any of a variety of materials through which a fluid is capable of passing, such as a fluidic channel, porous membrane, etc. For example, the chromatographic medium 23 may be a porous membrane formed from materials such as, but not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon);

porous gels, such as silica gel, agarose, dextran, and gelatin; polymeric films, such as polyacrylamide; and so forth. In one particular embodiment, the chromatographic medium is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The support 21 may be formed from any material able to carry the chromatographic medium 23. Although not required, the support 21 may be transparent so that light readily passes therethrough. In addition, it is also generally desired that the support 21 is liquid-impermeable so that fluid flowing through the medium does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. As is well known the art, the chromatographic medium 23 may be cast onto the support 21, wherein the resulting laminate may be die-cut to the desired size and shape. Alternatively, the chromatographic medium 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate structures are described in U.S. Pat. No. 5,075,077 to Durley, III, et al., which is incorporated herein in its entirety by reference thereto for all purposes.

The assay device 20 may also utilize an absorbent material 28. The absorbent material 28 generally receives fluid that has migrated through the entire chromatographic medium 23. As is well known in the art, the absorbent material 28 may assist in promoting capillary action and fluid flow through the medium 23.

The above-described incubation process may be conducted before applying the test sample to the chromatographic medium 23, or it may be incorporated as part of the assaying procedure (i.e., incubation occurs after the test sample is applied, such as within an incubation well). For instance, the incubation mixture may be directly applied to a portion of the chromatographic medium 23 through which it may then travel in the direction illustrated by arrow "L" in FIG. 1. Alternatively, the mixture may first be applied to a sample pad 22 or other material that is in fluid communication with the chromatographic medium 23. Some suitable materials that may be used to form the sample pad 22 include, but are not limited to, nitrocellulose, cellulose, porous polyethylene pads, and glass fiber filter paper. If desired, the sample pad 22 may also contain one or more assay pretreatment reagents, either diffusively or non-diffusively attached thereto.

Regardless, the chromatographic medium 23 defines a first detection zone 31 within which either a product conjugate or a substrate conjugate of the enzyme-catalyzed reaction may be captured and detected (e.g., indirectly). More specifically, the method utilized to capture a conjugate within the first detection zone 31 differentiates between the product conjugate and the substrate conjugate such that only one of the two is captured within the first detection zone 31. For instance, in one embodiment, the chromatographic medium 23 defines a first detection zone 31 within which a product conjugate may be captured and detected. The manner in which the product conjugates are captured may depend on the nature of the product of the enzyme-catalyzed reaction as well as on the nature of the reporters utilized. In some embodiments, a first receptive material may be immobilized within the first detection zone 31 for capturing product conjugates. In particular, a first receptive material may exhibit specific binding affinity for a product formed in the enzyme catalyzed reaction of the substrate. Accordingly, the first receptive material may be a first member of a specific binding pair, i.e., two different molecules where one of the molecules chemically and/or physically specifically binds to the second molecule, while the second member of the specific binding pair may be a product formed during the substrate/enzyme reaction that remains joined to the reporter. For instance, immunoreactive specific binding members may include antigens, haptens, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. Other common specific binding members include, but are not limited to, biotin and avidin, streptavidin, neutravidin, captavidin, or an anti-biotin antibody; protein A and G; carbohydrates and lectins, complementary nucleotide sequences (including probe and capture nucleic acid sequences used in DNA hybridization assays to detect a target nucleic acid sequence); complementary peptide sequences including those formed by recombinant methods; effector and receptor molecules; hormone and hormone binding protein; enzyme cofactors and enzymes, enzyme inhibitors and enzymes; derivatives thereof, and so forth. Furthermore, specific binding pairs may include members that are analogs, derivatives, and/or fragments of the original specific binding member. The details of the preparation of such antibodies and their suitability for use as specific binding members are well known to those skilled in the art.

In one particular embodiment, the substrate (e.g., a protein including free dicarboxylic acid residues, such as ovalbumin) may be methylated by a methylase in the presence of a suitable methyl source, such as S adenosyl-L-methyl methionine. The methylated product conjugate may become immobilized within the first detection zone 31 through specific binding between the methylated protein and a receptive material that exhibits specific binding affinity for the methylated protein. For example, the first receptive material may be a monoclonal antibody specific for the methylated protein. Upon immobilization of the product conjugate, a signal generated by the detectable substance (e.g., the reporter) may be detected.

In another embodiment, a kinase may be detected. For example, a protein kinase, such as Abl protein kinase, may be incubated with a substrate conjugate including a peptide sequence, such as SEQ ID NO.:1, joined to a reporter. In the presence of the kinase and a phosphate source, e.g., ATP, the peptide may be phosphorylated. Accordingly, the first receptive material may be a binding member specific for the SEQ ID NO.: 1 following the phosphorylation reaction, e.g., a monoclonal antibody and so forth.

Referring to FIG. 1, the diagnostic kit of the present invention may contain a second detection zone 35. Though illustrated as downstream of first detection zone 31, this is not a requirement of the present invention, and the second detection zone 35 may be either upstream or downstream of first detection zone 31. Within the second detection zone 35, either the substrate conjugates or the product conjugates may be captured and detected. For instance, when considering an embodiment in which the first detection zone 31 preferentially binds the product conjugates, the second detection zone 35 may be designed for capture of the substrate conjugates, and vice versa. Accordingly, within the second detection zone 35, the substrate conjugates and/or partially reacted complexes that do not bind to the first receptive material at the detection zone 31 may be captured and detected.

For example, a second receptive material may be immobilized within the second detection zone 35 that may serve as a stationary binding site for unreacted substrate conjugates, portions of the substrate released from the reporter during an enzyme-catalyzed cleavage reaction, and/or partially reacted complexes (e.g., reporter-substrate-enzyme complexes). The second receptive material may be any suitable binding agent that will exhibit differential binding with the substrate as compared to the product of the enzyme-catalyzed reaction, so as to differentiate the two. For example, the second receptive material may include binding members such as those described above. Because the second receptive material desirably binds specifically to the substrate conjugates, it will be different than the first receptive material. For example, while both materials may be of a similar type, e.g., monoclonal antibodies, the first receptive material will not bind the substrates, and the second receptive material will not bind the product of the enzyme-catalyzed reaction that remains joined to the reporter.

In the example described above, the substrate may be a protein including free dicarboxylic acid residues that may be targeted by a methylase and the second receptive material may be a specific binding member for the protein substrate (for example, a monoclonal antibody raised against the protein substrate). Similarly, when considering a substrate such as SEQ ID NO.: 1, the second receptive material may be a binding member that specifically binds to SEQ ID NO.: 1, for instance a monoclonal antibody raised against the polypeptide.

The first detection zone 31 and the optional second detection zone 35 may generally provide any number of distinct detection regions so that a user may better determine the concentration of an enzyme within a test sample. Each region with the detection zone 31, 35, may contain the same or different receptive materials. For example, the detection zone 31 may include two or more distinct detection regions (e.g., lines, dots, etc.). The use of two or more distinct detection regions may provide certain benefits, such as facilitating semi-quantitation and/or inhibiting potential false positives due to overrunning of the substrate conjugates or other materials. The detection regions with the zone may be disposed in the form of lines in a direction substantially perpendicular to the flow of the test sample through the chromatographic medium 23. Likewise, in some embodiments, the detection regions may be disposed in the form of lines in a direction substantially parallel to the flow of the test sample through the medium 23.

In those embodiments in which the first detection zone 31 is designed for capturing the product conjugates, as the enzyme concentration begins to increase in the test sample, more product conjugates are formed that have specific binding affinity for the receptive material at the first detection zone 31. The increased quantity of reporters at the first detection zone 31 thus results in an increase in signal intensity. From this increase in signal intensity, the presence or concentration of the enzyme may be readily determined. For example, in one embodiment, the amount of enzyme is directly proportional to the signal intensity at the first detection zone 31, $I_1$. If desired, the signal intensity $I_1$ may be plotted versus the enzyme concentration for a range of known enzyme concentrations to generate an intensity curve. To determine the quantity of enzyme in an unknown test sample, the signal intensity may then be converted to enzyme concentration according to the intensity curve.

It should be understood that one or more distinct regions of the first detection zone 31 may exhibit the above-described relationship between signal intensity and enzyme concentration; however, each distinct region need not exhibit such a relationship. For example, in some embodiments, only one of multiple distinct regions may exhibit a signal intensity that is directly proportional to the concentration of the enzyme. The signal intensity of other distinct regions, such as those used to reduce false positives, may otherwise remain constant, or exhibit an increase and/or decrease in signal intensity. So long as at least one distinct region of the detection zone 31 satisfies the direct relationship, the signal intensity exhibited by the first detection zone 31 is considered directly proportional to the enzyme concentration.

In accordance with the present invention, the level of detection sensitivity for the enzyme of interest may be selectively controlled depending on the desired application. One particular technique for controlling the detection sensitivity involves manipulating the quantity of the first receptive material used in the first detection zone 31. For instance, when assaying samples suspected of containing large concentrations of an enzyme, the quantity of the first receptive material may be equal to or greater than the minimum required to capture the total quantity of product conjugates that may be formed by the enzyme-catalyzed reaction. Thus, if a particular amount of enzyme were present in the test sample, a very high percentage of the substrate conjugates would react with the enzyme to form product conjugates that may be immobilized at the detection zone 31 and essentially all of the reporters would be present within the first detection zone 31. The minimum quantity required to capture a high percentage of the product conjugates may be determined experimentally, and generally depends upon the reactivity of the substrate with the enzyme.

In applications where enhanced detection sensitivity is desired (e.g., low suspected enzyme concentrations or short incubation times), the quantity of the first receptive material may be more than the minimum required to capture the total quantity of product conjugates utilized. The use of a large quantity of the first receptive material may provide a variety of benefits, including increasing the likelihood that any partially reacted complexes are captured at the first detection zone 31, which would otherwise result in a measured enzyme concentration that is slightly lower than the actual concentration. That is, the partially reacted complexes generally will be less likely to bind to the receptive materials due to steric hindrance, etc., as compared to product conjugates that are completely reacted. This statistically decreases the chance that the partially reacted complexes will bind to the first detection zone 31.

When the substrate conjugates are directly detectable at the second detection zone 35, a decrease in enzyme concentration results in an increase in the signal intensity at the second detection zone 35, $I_2$, due to the presence of substrate conjugates and/or partially reacted complexes. From this increase in signal intensity, the presence or concentration of the enzyme may be readily determined. For example, in one embodiment, the amount of enzyme is inversely proportional to the signal intensity at the second detection zone 35, $I_2$. If desired, the signal intensity $I_2$ may be plotted versus the enzyme concentration for a range of known enzyme concentrations to generate an intensity curve. To determine the quantity of enzyme in an unknown test sample, the signal intensity may then be converted to enzyme concentration according to the intensity curve. It should be understood that, as discussed above with respect to the first detection zone 31, so long as one distinct region of the second detection zone 35 satisfies the inverse relationship, the signal intensity exhibited by the second detection zone 35 is considered inversely proportional to the enzyme concentration.

Also, an inverse relationship may exist between the signal intensity at the first detection zone 31 ($I_1$) and the second detection zone 35 ($I_2$). For example, because a predetermined amount of reporters are present, the amount captured at the second detection zone 35 is inversely proportional to the amount captured at the first detection zone 31. As a result of this inverse relationship, the concentration of the enzyme may, in some cases, be more effectively measured over an extended range by comparing the signal intensity at both detection zones. For example, in one embodiment, the amount of enzyme is directly proportional to the ratio of the signal intensity "$I_1$" to the signal intensity "$I_2$." Based upon the range in which this ratio falls, the general concentration range for the enzyme may be determined. If desired, the ratio of $I_1$ to $I_2$ may be plotted versus enzyme concentration for a range of known enzyme concentrations to generate an intensity curve. To determine the quantity of enzyme in an unknown test sample, the signal intensity ratio may then be converted to enzyme concentration according to the intensity curve. It should be noted that alternative mathematical relationships between $I_1$ and $I_2$ may be plotted versus the enzyme concentration to generate the intensity curve. For example, in one embodiment, the value of $I_1/(I_1+I_2)$ may be plotted versus enzyme concentration to generate the intensity curve.

As stated above, certain embodiments of the present invention may utilize a reporter that is not directly detectable. Thus, when released, it is generally desired that the reporter interact in some manner with a detectable substance for subsequent detection. For example, probes capable of generating a detectable signal may be employed that are configured to bind to the product conjugates and/or substrate conjugates that include the reporters. For example, probes may contain particles labeled or otherwise applied with the detectable substance. In some instances, it is desired to modify the probes in some manner. For example, the probes may be modified with a specific binding member to form conjugated probes that have specific affinity for the product conjugates. The specific binding members may generally be conjugated to the probes using any of a variety of well-known techniques, such as through covalent bonding and/or physical adsorption in a manner such as described above. In one particular embodiment, carboxylic groups on the probe surface are activated and reacted with amino groups of the specific binding member to form an amide bond. When utilized, it is generally desired that the specific binding pair used for the probes and reporter is different than the specific binding pair used for the first receptive material and the second receptive material. This helps to ensure that the probes and reporters do not substantially interfere with the binding mechanism described above.

The probes may be contacted with the product conjugates and/or the substrate conjugates at any stage of the enzyme detection process. For example, in some embodiments, the probes may be applied to the assay device 20 at a location upstream from the region in which detection is desired. For example, in one embodiment, the probes may be applied to a conjugated pad (not shown) that is located upstream from the detection zones 31 and 35, but downstream from the sample pad 22.

In such embodiments, a variety of assay formats may be used to detect the product conjugates. In one embodiment, for example, a "sandwich" assay format is utilized in which the product conjugate has an affinity for the specific binding member of the conjugated probe as well as for the second receptive material. The product conjugate, including, e.g., antibodies, antigens, etc., typically has two or more binding sites (e.g., epitopes). One of these binding sites becomes occupied by the specific binding member of the conjugated probe. However, the free binding site of the product conjugate may subsequently bind to a receptive material immobilized within the first detection zone 31 to form a new ternary sandwich complex. Alternatively, the product conjugate may be detected using direct or indirect "competitive" assay formats. In such instances, the specific binding member of the conjugated probe may be the same as or an analog of the product conjugate. Thus, upon reaching the first detection zone 31, the conjugated detection probes and the product conjugate compete for available binding sites of the immobilized receptive material. Of course, any other assay format is also suitable for use in the present invention.

For the embodiments described above in which the product conjugates are indirectly detectable, an increase in enzyme concentration within the test sample results in the formation in a greater number of product conjugates. Thus, if a sandwich assay format is used, more product conjugates bind to the conjugated probes so that the amount of enzyme is directly proportional to the signal intensity at the first detection zone 31. On the other hand, if a competitive assay format is used, the amount of enzyme is inversely proportional to the signal intensity at the first detection zone 31. In any event, the signal intensity may be plotted versus the enzyme concentration for a range of known enzyme concentrations to generate an intensity curve. To determine the quantity of enzyme in an unknown test sample, the signal intensity may then be converted to enzyme concentration according to the intensity curve.

Figure 3:
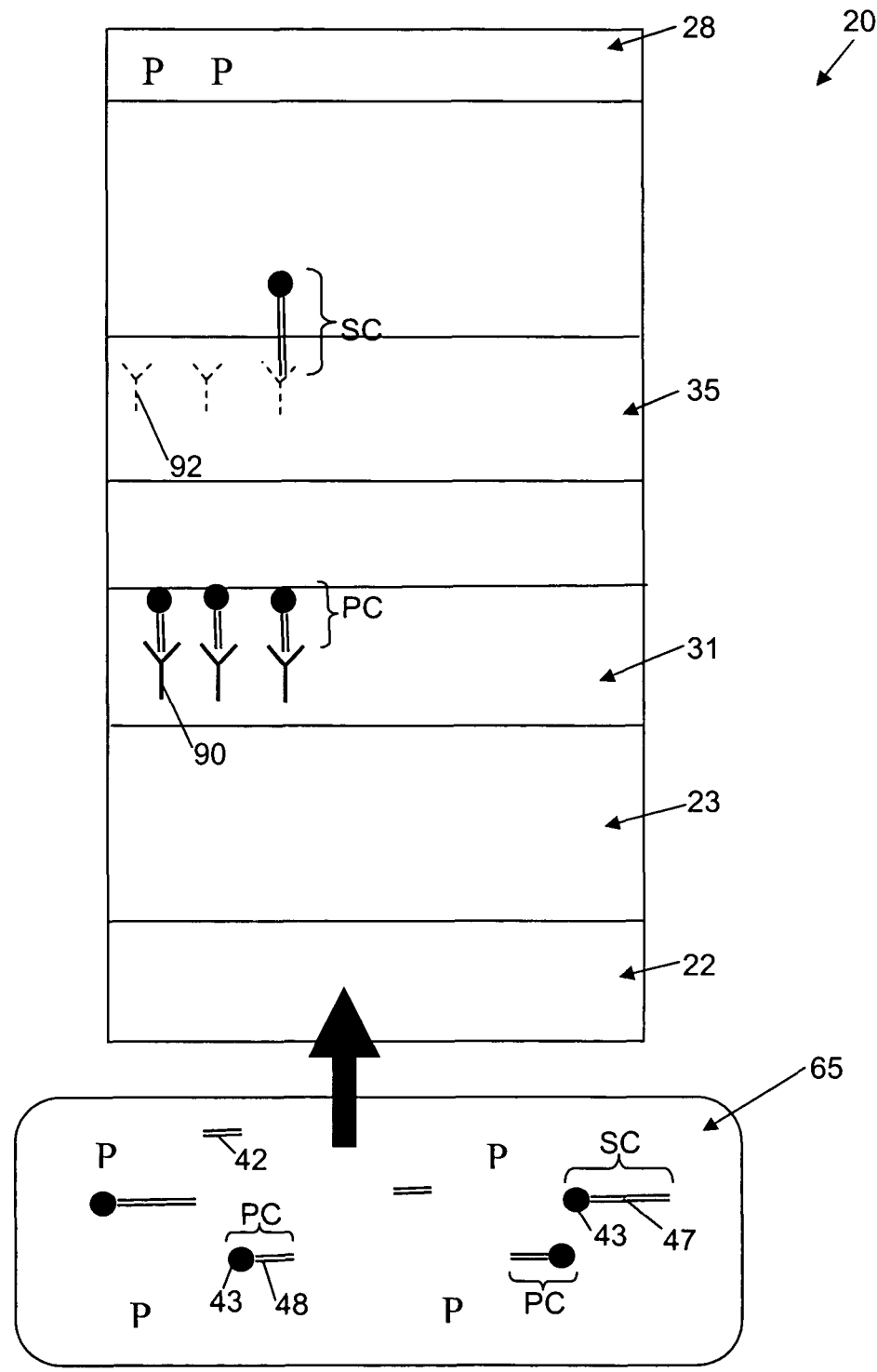
FIG. 3 is a schematic illustration of one assaying technique that may be used in one embodiment of the present invention to detect the presence or quantity of an enzyme within a test sample.

Referring to FIG. 3, one embodiment of a method for detecting the presence of a protease using fluorescence will now be described in more detail. Initially, a test sample containing a protease P is mixed with substrate conjugates SC that each include a fluorescent particle 43 joined to a substrate 47 (e.g., protein or glycoprotein). The substrate conjugates SC are allowed to incubate with the protease P for a sufficient period of time to form an incubation mixture (designated numeral 65 in FIG. 3) that includes polypeptides cleaved from the substrate 42 via the enzyme-catalyzed reaction, unreacted substrate conjugates SC, protease P, and product conjugates PC generated by the enzyme-catalyzed reaction that each include a fluorescent particle 43 joint to the product 48 generated via the enzyme-catalyzed reaction. The incubation mixture 65 is applied to the sample pad 22, as indicated by the illustrated directional arrow, and then travels to the first detection zone 31. Immobilized within first detection zone 31 is a first receptive material 90 that is specific for the products 48 generated by the enzyme-catalyzed reaction. Thus, the available binding sites in the first detection zone 31 may be occupied by the product conjugates PC. However, substrate conjugates SC travel to a second detection zone 35 and bind to a second receptive material 92 contained therein that is a specific binding member for the unreacted substrates 47. The fluorescent particles 43 joined to the substrates 47 therefore also travel to the second detection zone 35 and bind to the second receptive material.

Once captured, the signal intensity of the fluorescent particles 43 may be measured at the first detection zone 31 and/or the second detection zone 35. Fluorescence detection generally utilizes wavelength filtering to isolate the emission photons from the excitation photons, and a detector that registers emission photons and produces a recordable output, usually as an electrical signal or a photographic image. One suitable fluorescence detector for use with the present invention is a FluoroLog III Spectrofluorometer, which is sold by SPEX Industries, Inc. of Edison, N.J. Another example of a suitable fluorescence detector is described in U.S. Patent Application Publication No. 2004/0043502 to Song, et al., which is incorporated herein in its entirety by reference thereto for all purposes. Although the use of fluorescence is utilized in this particular embodiment, it should be understood that any other known detection technique may also be utilized in the present invention. For example, other suitable optical detection techniques may include, but not limited to, phosphorescence, diffraction, reflectance, transmittance, etc. The optical reader may be capable of emitting light and also registering a detection signal (e.g., transmitted or reflected light, emitted fluorescence or phosphorescence, etc.). For example, in one embodiment, a reflectance spectrophotometer or reader may be utilized to detect the presence of reporters that exhibit a visual color (e.g. dyed latex microparticles). One suitable reflectance reader is described, for instance, in U.S. Patent App. Pub. No. 2003/0119202 to Kaylor, et al., which is incorporated herein in its entirety by reference thereto for all purposes.

Regardless of the technique used to measure signal intensity, the absolute amount of the protease P may be ascertained by comparing the signal intensity at the first detection zone 31 with the signal intensity at the second detection zone 35. For example, as indicated above, the amount of the protease P may be determined by the ratio $I_1/I_2$, and converting this ratio to an enzyme concentration using a previously ascertained intensity curve. Alternatively, the signal intensities $I_1$ or $I_2$ may also be used independently to indicate the presence or concentration of the enzyme. Of course, the present invention also contemplates qualitative embodiments in which the mere presence of the enzyme is confirmed by signal intensity without a particular correlation to an actual enzyme concentration.

Figure 4:
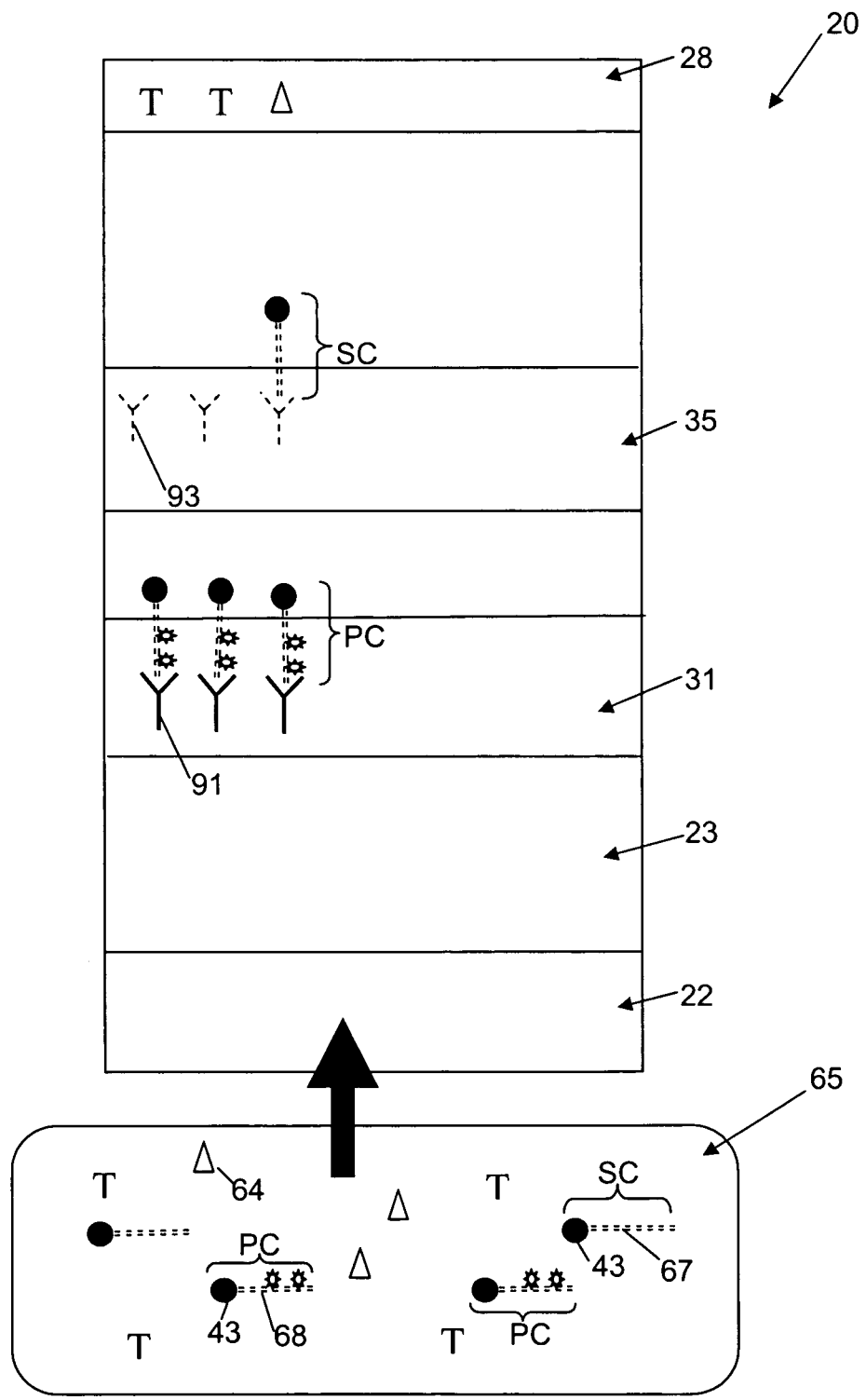
FIG. 4 is a schematic illustration of another assaying technique that may be used in another embodiment of the present invention to detect the presence or quantity of an enzyme within a test sample.

Referring to FIG. 4, one embodiment of a method for detecting the presence of a transferase using fluorescence will now be described in more detail. Initially, a test sample containing a transferase T is mixed with substrate conjugates SC that each include a fluorescent particle 43 joined to a substrate 67 (e.g., a polypeptide). The substrate conjugates SC are allowed to incubate with the transferase for a sufficient period of time to form an incubation mixture (designated numeral 65 in FIG. 4) that includes components 64 (e.g., ATP) that may provide the moiety targeted by the transferase, unreacted substrate conjugates SC, transferase T, and product conjugates PC generated by the enzyme-catalyzed reaction that each include a fluorescent particle 43 joined to the product 68 generated via the enzyme catalyzed reaction (e.g., the phosphorylated polypeptide). The incubation mixture 65 is applied to the sample pad 22, as indicated by the illustrated directional arrow, and then travels to the first detection zone 31. Immobilized within first detection zone 31 is a first receptive material 91 that is specific for the product 68 generated by the enzyme-catalyzed reaction. Thus, the available binding sites in the first detection zone 31 may be occupied by the product conjugates PC. However, unreacted substrate conjugates SC travel to a second detection zone 35 and bind to a second receptive material 93 contained therein that is a specific binding member for the unreacted substrates 67. The fluorescent particles 43 joined to the substrates 67 therefore also travel to the second detection zone 35 and bind to the second receptive material. Once captured, signal intensity may be measured and analyzed as described for other embodiments described herein.

In one exemplary application, the diagnostic kit may be used for determining the presence of enzymes involved in the RAS protein activation cycle. RAS proteins function as important molecular switches for a wide variety of signal pathways. These pathways control processes including cytoskeleton integrity, cell adhesion and migration, and apoptosis. RAS proteins cycle between an activated form (RAS-GTP) and an inactivated form (RAS-GDP).

RAS proteins are often deregulated in cancers, leading to increased invasion and metastasis as well as decreased apoptosis. Accordingly, the diagnostic kit may be utilized for determination of the presence of GTPase-activating proteins (GAPs) that increase the rate of GTP hydrolysis, returning RAS-GTP to its inactive RAS-GDP form. For instance, a test sample containing a GAP may be mixed with substrate conjugates that each include a fluorescent particle joined to an RAS-GTP substrate. The substrate conjugates are allowed to incubate with the test sample for a sufficient period of time to form an incubation mixture that may include unreacted substrate conjugates (RAS-GTP/particle), GAP, and product conjugates generated by the enzyme-catalyzed reaction (RAS-GDP/particle). The incubation mixture is applied to the sample pad, as described above, and then travels to a detection zone. Immobilized within the detection zone is a receptive material that is specific for either the product RAS-GDP generated by the enzyme-catalyzed reaction or optionally for the substrate RAS-GTP. For example, within the detection zone may be immobilized a MAP kinase that is activated by RAS-GTP in certain metabolic pathways. Thus, the available binding sites in the detection zone may be occupied by substrate conjugates (RAS-GTP/particle) that preferentially bind the MAP kinase receptive material. The fluorescent particles joined to the substrates therefore will also be bound in the detection zone. However, product conjugates (RAS-GDP/particle) do not preferentially bind the MAP kinase receptive material and may pass through the detection zone. Once captured, signal intensity may be measured and analyzed as described for other embodiments described herein to determine the presence of GAPs in the test sample.

In another embodiment, a diagnostic test kit may be utilized to determine the presence of RAS activating proteins. For instance, the diagnostic test kit may be utilized to determine the presence of G exchange factors (GEF) (e.g., CDC25, SOS1, SOS2) that catalyze the reactivation of RAS-GDP to its active form, RAS-GTP. According to this embodiment, the substrate conjugates may include the inactive form of the protein, RAS-GDP, joined to the fluorescent particle. Upon incubation of the substrate conjugates with the test sample containing the activating GEF, the RAS-GDP may be activated to the RAS-GTP form. In this case, the product conjugates (RAS-GTP/particle) may be captured by the MAP kinase immobilized in the detection zone to determine the presence or quantity of GEF in the test sample.

Another exemplary application of the diagnostic test kit may be in the determination of the presence of angiotensin-converter enzyme (ACE) in a test sample. ACE is an exopeptidase that catalyzes the conversion of angiotensin I to angiotensin II. While angiotensin I appears to exist primarily as a precursor to angiotensin II, angiotensin II is a potent vasoconstrictor and believed to play a role in conditions such as high blood pressure, heart disease and diabetic nephropathy. According to this particular embodiment, the diagnostic test kit may include substrate conjugates including angiotensin I joined to a reporter. Upon incubation of the substrate conjugates with the test sample containing ACE, the angiotensin I may be converted to angiotensin II. The detection zone of the diagnostic test kit may contain immobilized therein a receptive material that is specific for angiotensin II, such as $AT_1$ or $AT_2$ receptors, for example. The binding and detection of the product conjugates (angiotensin II/reporter) in the detection zone may indicate the presence of ACE in the test sample.

The diagnostic kit of the present invention may contain other zones, in addition to the detection zones 31, 35 described above. For instance, the assay device may optionally include a calibration zone. In this embodiment, the calibration zone (not shown) is formed on the membrane 23 and is positioned downstream from the detection zone 31 and optional detection zone 35. Alternatively, however, the calibration zone may also be positioned upstream from the detection zone 31 and/or optional detection zone 35. The calibration zone is provided with a receptive material that is capable of binding to any calibration probes that pass through the length of the membrane 23. When utilized, the calibration probes may contain a detectable substance that is the same or different than the detectable substance used for the substrate conjugates and the product conjugates. Moreover, the calibration probes may also be conjugated with a specific binding member, such as described above. For example, in one embodiment, biotinylated calibration probes may be used. Generally speaking, the calibration probes are selected in such a manner that they do not bind to the first or second receptive material at the detection zone 31 and detection zone 35. The receptive material of the calibration zone may be the same or different than the receptive materials used in the detection zone 31 or detection zone 35. For example, in one embodiment, the receptive material of the calibration zone is a biological receptive material, such as antigens, haptens, antibody-binding proteins (e.g., protein A, protein G, or protein A/G), neutravidin, avidin, streptavidin, captavidin, primary or secondary antibodies, or complexes thereof. It may also be desired to utilize various non-biological materials for the receptive material (e.g., polyelectrolytes) of the calibration zone, such as described in U.S. Patent Application Publication No. 2003/0124739 to Song. et al., which is incorporated herein in its entirety by reference thereto for all purposes.

When utilized, the polyelectrolytes may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethyleneimine; epichlorohydrin-functionalized polyamines and/or polyamidoamines, such as poly(dimethylamine-co-epichlorohydrin); polydiallyidimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridnium iodide) and poly (styryl-b-acrylic acid), both of which are available from Polymer Source, Inc. of Dorval, Canada.

Although any polyelectrolyte may generally be used, the polyelectrolyte selected for a particular application may vary depending on the nature of the substrate conjugates, product conjugates, the calibration probes, the membrane, and so forth. In particular, the distributed charge of a polyelectrolyte allows it to bind to substances having an opposite charge. Thus, for example, polyelectrolytes having a net positive charge are often better equipped to bind with probes that are negatively charged, while polyelectrolytes that have a net negative charge are often better equipped to bind to probes that are positively charged. Thus, in such instances, the ionic interaction between these molecules allows the required binding to occur within the calibration zone. Nevertheless, although ionic interaction is primarily utilized to achieve the desired binding in the calibration zone, polyelectrolytes may also bind with probes having a similar charge.

Because the polyelectrolyte is designed to bind to probes, it is typically desired that the polyelectrolyte be substantially non-diffusively immobilized on the surface of the membrane 23. Otherwise, the probes would not be readily detectable by a user. Thus, the polyelectrolytes may be applied to the membrane 23 in such a manner that they do not substantially diffuse into the matrix of the membrane 23. In particular, the polyelectrolytes typically form an ionic and/or covalent bond with functional groups present on the surface of the membrane 23 so that they remain immobilized thereon. Although not required, the formation of covalent bonds between the polyelectrolyte and the membrane 23 may be desired to more permanently immobilize the polyelectrolyte thereon. For example, in one embodiment, the monomers used to form the polyelectrolyte are first formed into a solution and then applied directly to the membrane 23. Various solvents (e.g., organic solvents, water, etc.) may be utilized to form the solution. Once applied, the polymerization of the monomers is initiated using heat, electron beam radiation, free radical polymerization, and so forth. In some instances, as the monomers polymerize, they form covalent bonds with certain functional groups of the membrane 23, thereby immobilizing the resulting polyelectrolyte thereon. For example, in one embodiment, an ethyleneimine monomer may form a covalent bond with a carboxyl group present on the surface of some membranes (e.g., nitrocellulose).

In another embodiment, the polyelectrolyte may be formed prior to application to the membrane 23. If desired, the polyelectrolyte may first be formed into a solution using organic solvents, water, and so forth. Thereafter, the polyelectrolytic solution is applied directly to the membrane 23 and then dried. Upon drying, the polyelectrolyte may form an ionic bond with certain functional groups present on the surface of the membrane 23 that have a charge opposite to the polyelectrolyte. For example, in one embodiment, positively-charged polyethyleneimine may form an ionic bond with negatively-charged carboxyl groups present on the surface of some membranes (e.g., nitrocellulose).

In addition, the polyelectrolyte may also be crosslinked to the membrane 23 using various well-known techniques. For example, in some embodiments, epichlorohydrin-functionalized polyamines and/or polyamidoamines may be used as a crosslinkable, positively-charged polyelectrolyte. Examples of these materials are described in U.S. Pat. No. 3,700,623 to Keim and U.S. Pat. No. 3,772,076 to Keim, U.S. Pat. No. 4,537,657 to Keim, which are incorporated herein in their entirety by reference thereto for all purposes and are believed to be sold by Hercules, Inc., Wilmington, Del. under the Kymene™ trade designation. For instance, Kymene™ 450 and 2064 are epichlorohydrin-functionalized polyamine and/ or polyamidoamine compounds that contain epoxide rings and quaternary ammonium groups that may form covalent bonds with carboxyl groups present on certain types of membranes (e.g., nitrocellulose) and crosslink with the polymer backbone of the membrane when cured. In some embodiments, the crosslinking temperature may range from about 50° C. to about 120° C. and the crosslinking time may range from about 10 to about 600 seconds.

Although various techniques for non-diffusively immobilizing polyelectrolytes on the membrane 23 have been described above, it should be understood that any other technique for non-diffusively immobilizing polyelectrolytic compounds may be used in the present invention. In fact, the aforementioned methods are only intended to be exemplary of the techniques that may be used in the present invention. For example, in some embodiments, certain components may be added to the polyelectrolyte solution that may substantially inhibit the diffusion of such polyelectrolytes into the matrix of the membrane 23.

In some cases, the membrane 23 may also define a control zone (not shown) that gives a signal to the user that the assay is performing properly. For instance, the control zone (not shown) may contain an immobilized receptive material that is generally capable of forming a chemical and/or physical bond with probes or with the receptive material immobilized on the probes. Some examples of such receptive materials include, but are not limited to, antigens, haptens, antibodies, protein A or G, avidin, streptavidin, secondary antibodies, and complexes thereof. In addition, it may also be desired to utilize various non-biological materials for the control zone receptive material. For instance, in some embodiments, the control zone receptive material may also include a polyelectrolyte, such as described above, that may bind to uncaptured probes. Because the receptive material at the control zone is only specific for probes, a signal forms regardless of whether the analyte is present. The control zone may be positioned at any location along the membrane 23, but is preferably positioned downstream from the detection zone 31 and the detection zone 35.

The aforementioned detection techniques are described specifically in the context of enzymes. However, as stated, the present invention is equally suitable for detecting the presence or quantity of an enzyme inhibitor within a test sample. To detect the presence of an enzyme inhibitor within a test sample, a predetermined quantity of a corresponding enzyme may be mixed with the test sample and allowed to incubate. In the presence of a certain amount of an enzyme inhibitor, the enzyme-catalyzed reaction does not proceed at a detectable rate. Thus, the relationship between enzyme inhibitor concentration and signal intensity will be opposite to the relationship between enzyme concentration and signal intensity. As an illustration, an enzyme-catalyzed reaction will not occur in the presence of a certain amount of inhibitor. Thus, no product conjugates will be captured at the detection zone 31, which generates its minimum signal intensity. On the other hand, as the amount of enzyme inhibitor is reduced, the enzyme causes the product conjugates to form as described above. The signal intensity generated at the detection zone 31 thus begins to increase due to a corresponding increase in the presence of product conjugates. Likewise, the signal intensity generated at the detection zone 35 may, in some embodiments, begin to decrease due to a corresponding decrease in the presence of substrate conjugates. Accordingly, in this particular embodiment, the amount of enzyme inhibitor within the test sample is inversely proportional to the signal intensity at the detection zone 31 and directly proportional to the signal intensity at the detection zone 35.

The diagnostic test kit of the present invention may provide a relatively simple and cost-efficient method to quickly perform on-site testing of enzymes or their inhibitors. The test kit may provide a test result that is visible so that it is easily observed by the person performing the test in a prompt manner and under test conditions conducive to highly reliable and consistent test results. The diagnostic test kit is also disposable so that, if desired, it may be discarded when the test is concluded.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for detecting an enzyme, or an inhibitor thereof, within a test sample, the method comprising:
   contacting a test sample with a plurality of substrate conjugates to form an incubation mixture that includes the substrate conjugates and the test sample, said substrate conjugates each comprising a substrate joined to a reporter, wherein an enzyme-catalyzed reaction of said substrate conjugate forms a product conjugate, said product conjugate comprising a product of the enzyme-catalyzed reaction joined to the reporter, said reporter being capable of directly or indirectly generating an optically detectable detection signal;
   applying said incubation mixture to a chromatographic medium, said chromatographic medium comprising a first detection zone within which said product conjugate preferentially binds, said chromatographic medium further comprising a second detection zone within which said substrate conjugate preferentially binds, said incubation mixture migrating through said chromatographic medium to reach said first detection zone and said second detection zone, wherein the binding of the product conjugate generates a first detection signal within said first detection zone, and wherein the binding of the substrate conjugate generates a second detection signal within said second detection zone; and optically determining the presence or intensity of said first detection signal within said first detection zone and said second detection signal within said second detection zone.

2. The method of claim 1, wherein the amount of an enzyme within said test sample is inversely proportional to the intensity of said second detection signal in said second detection zone.

3. The method of claim 1, wherein the amount of an enzyme within said test sample is directly proportional to the intensity of said first detection signal in said first detection zone.

4. The method of claim 1, wherein the enzyme is a hydrolase.

5. The method of claim 1, wherein the enzyme is a transferase, a ligase, or a polymerase.

6. The method of claim 5, wherein the transferase is a kinase or a methylase.

7. The method of claim 1, wherein said substrate is a protein, glycoprotein, peptide, nucleic acid, carbohydrate, lipid, ester, antibody, antigen, or a derivative thereof.

8. The method of claim 7, wherein said substrate is casein, albumin, hemoglobin, myoglobin, keratin, gelatin, insulin, proteoglycan, fibronectin, laminin, collagen, elastin, or a derivative thereof.

9. The method of claim 1, wherein product conjugate and unreacted substrate conjugate are capable of reaching said first detection zone.

* * * * *